United States Patent [19]
Zviak et al.

[11] 3,988,110
[45] Oct. 26, 1976

[54] HAIR COLORING AND HAIR-SETTING LOTION CONTAINING A DIRECT DYE, A REDUCING AGENT AND A SOLAR FILTER

[75] Inventors: Charles Zviak, Franconville; Giuliana Ghilardi, Paris, both of France

[73] Assignee: Societe Anonyme dite: L'Oreal, Paris, France

[22] Filed: May 20, 1975

[21] Appl. No.: 579,050

Related U.S. Application Data

[60] Division of Ser. No. 405,869, Oct. 12, 1973, Pat. No. 3,906,091, which is a continuation-in-part of Ser. No. 100,840, Dec. 22, 1970, abandoned.

[30] Foreign Application Priority Data

Dec. 24, 1969  Luxemburg ............................ 60093

[52] U.S. Cl. .......................................... 8/10.1; 8/10; 8/10.2; 8/11; 424/DIG. 2; 424/70; 424/71
[51] Int. Cl.² ............................................. A61K 7/13
[58] Field of Search .................. 424/71, DIG. 2, 70; 8/10, 10.1, 11, 10.2

[56] References Cited
UNITED STATES PATENTS

| | | | |
|---|---|---|---|
| 3,011,950 | 12/1956 | Mehaffey | 424/59 X |
| 3,068,151 | 12/1962 | Haefele | 424/71 |
| 3,133,865 | 5/1964 | Richardson | 424/71 |
| 3,215,604 | 11/1965 | Biamonte | 424/71 |
| 3,218,234 | 11/1965 | Wilmsmann et al. | 424/70 |
| 3,406,238 | 10/1968 | Freyermuth et al. | 424/59 X |

*Primary Examiner*—Leonard Schenkman
*Assistant Examiner*—Vera C. Clarke
*Attorney, Agent, or Firm*—Cushman, Darby & Cushman

[57] ABSTRACT

A hair coloring and hair-setting lotion composition comprises in combination an aqueous solution of a lower alkanol, a cosmetic film-forming resin, a direct dye, a solar filter and a reducing agent selected from the group consisting of butyl hydroxy anisole, dodecyl gallate, propyl gallate and octyl gallate. The reducing agent is generally present in amounts of about 0.02 – 2% by weight of the composition.

5 Claims, No Drawings

HAIR COLORING AND HAIR-SETTING LOTION CONTAINING A DIRECT DYE, A REDUCING AGENT AND A SOLAR FILTER

This is a division of application Ser. No. 405,869 filed Oct. 12, 1973, now U.S. Pat. No. 3,906,091 which is a continuation-in-part of Ser. No. 100,840, filed Dec. 22, 1970, now abandoned.

This invention relates to hair-setting lotions intended essentially for hair having undergone an oxidizing treatment, this oxidizing treatment being able to be either a bleaching operation or a dyeing with oxidization dyes.

It is known that oxidizing agents used during bleaching or oxidation dyeing, and in particular hydrogen peroxide, damage the keratinous fibers, so that hair subjected to such oxidizing treatments quickly becomes porous, fragile and brittle.

It is also known that these oxidizing agents, and in particular hydrogen peroxide, penetrate in small amounts into the hair during treatment. Consequently, after treatment, traces of the oxidizing agent remain in the hair which ordinary rinsing, careful as it might be, cannot entirely eliminate.

In the case of bleached hair, the presence of these traces of oxidizing agent constitute a threat to the holding of further dyeing to which the hair is usually subjected, this oxidizing agent contributing to the destructive action of the air and light in regard to the dyeing. For the same reason, in the case of oxidization dyeings the coloring of the hair often fades rather rapidly in time.

From what has been said, it can be seen how important it is to eliminate these traces of the oxidizing agent, or at least to prevent their destructive action in regard to dyes applied simultaneously or later to the hair.

In an attempt to remove hydrogen peroxide residue from human hair several agents have been suggested in the prior art. For instance, catalase was suggested (Swiss Pat. No. 264,760) as well as thiourea, thiosulfates, dithionite, hypophosphite and ascorbic acid. Further, U.S. Pat. No. 3,218,234 which discloses the disadvantages of employing the above referred to agents, teaches the use of an α-carbonyl monocarboxylic acid such as pyruvic acid and glyoxylic acid. It has been found however that the use of a composition containing such an acid, for instance, pyruvic acid, does not provide the uniformity of a subsequent dyeing operation as is achieved when the hair containing residual peroxide values is treated with the composition of the present invention.

For this purpose a hair-setting lotion intended for bleached hair and hair having undergone dyeing with oxidation dyes has now been developed, this hair-setting lotion being characterized by the presence therein of an agent which protects the dye by neutralizing the oxidizing agent present in the fiber.

Thus one object of the present invention is the provision of a method for treating peroxide-containing human hair for neutralizing the peroxide therein comprising contacting said peroxide-containing hair with a member selected from the group consisting of butylhydroxy anisole, dodecyl gallate, propyl gallate and octyl gallate in amounts effective to neutralize said peroxide.

The present invention also has for an object a hair-setting lotion characterized by the fact that it comprises an aqueous solution of a lower alkanol, a cosmetic film-forming resin and at least one organic reducing compound of the substituted phenol family, selected from the group consisting of butylhydroxy anisole, dodecyl gallate, isopropyl gallate and octyl gallate.

The amount of reducing agent used in the compositions according to the invention can vary from about 0.02 to about 2% by weight and preferably from about 0.05 to about 0.5% by weight.

The pH of the compositions according to the invention can vary within broad limits. However, the pH generally ranges between 5 and 8.5.

The cosmetic film-forming resin employed in the composition of this invention can be any of those conventionally employed in hair-setting lotions. Generally such cosmetic film-forming resins have a molecular weight ranging from about 10,000–400,000, or even higher.

Representative cosmetic film-forming resins that can be employed include polyvinylpyrrolidone having a molecular weight of 40,000–400,000; copolymer of vinylpyrrolidone and vinyl acetate, 70%:30% to 30%:70% having a molecular weight of 40,000–400,000; copolymer of vinyl acetate and an unsaturated carboxylic acid such as crotonic acid, 90%:10% having a molecular weight of 45,000 to 70,000; copolymer resulting from the polymerization of vinyl acetate (75–85%), crotonic acid (5–15%) and an acrylic or methacrylic ester (5–15%) or an alkylvinyl ether (5–15%); copolymer resulting from the copolymerization of vinyl acetate (63–88%), crotonic acid (5–15%) and (a) a vinyl ester of a long carbon chain acid having 10–22 carbon atoms or (b) an alkyl or methalkyl ester of a long carbon chain acid having 10–22 carbon atoms (5–25%); copolymer resulting from the copolymerizaton of an ester derived from an unsaturated alcohol having 2–12 carbon atoms and a saturated short chain carboxylic acid having 2–5 carbon atoms (65–80%) and an unsaturated acid having 4–20 carbon atoms (7–12%) and at least one ester derived from a saturated alcohol having 8–18 carbon atoms and an unsaturated acid having 4–20 carbon atoms (10–20%) and a copolymer resulting from the polymerization of at least an unsaturated ester and at least an unsaturated acid. The cosmetic film forming resin is used in amounts of about 1–3 percent by weight of said composition.

Suitable alcohols employed in the compositions according to the invention are low molecular weight alcohols and preferably lower alkanols having 1–4 carbon atoms such as ethanol or isopropanol. These alcohols are used in amounts of about 20 to 50% by weight of the total composition.

The hair-setting lotions according to the invention can also contain direct dyes, for example, nitro dyes, disperse dyes, anthraquinone dyes, azo dyes, metalliferous dyes, acid dyes or basic dyes.

These dyes can be introduced into the compositions according to the invention in variable amounts the proportions used depending on the intensity of the color desired. However, the concentration of dyes can vary most often between about 0.001 and 0.1% by weight of the total composition.

The composition according to the invention can also contain solar filters which are intended to protect, against the action of light, the dyes that they contain or those already applied to the hair. Representative solar filters include, for example benzylidene camphor, glyceryl para-amino benzoate, benzophenone or ethyl paradimethylaminobenzoate. These solar filters are incorporated in compositions according to the invention in amounts of about 0.03 to 2% by weight of the total composition.

Finally, the compositions according to the invention can contain various ingredients usually used in cosmetics, such as wetting agents, dispersing agents, swelling agents, penetrating agents, softeners or perfumes, and even materials which can reduce excessive secretion or sebum from the skin or scalp.

The hair-setting lotions according to the invention are applied in a conventional manner to wet hair, which is then rolled up and dried.

The compositions according to the invention can be applied either on the day of dyeing or bleaching treatment, or several days or weeks after this treatment, for instance, during a hair-setting operation.

EXAMPLE 1

A hair-setting lotion having the following composition is prepared:

| | |
|---|---|
| Crotonic acid/vinyl acetate copolymer, 10%/90% (M.W. 45,000 to 70,000) | 2 g |
| Ethanol sufficient for 50° titer | |
| Triethanolamine sufficient for pH 5.5 | |
| Benzylidene camphor | 0.2 g |
| Butylhydroxyanisole: (Mixture of 4-hydroxy 3-t-butylanisol and 4-hydroxy 2-t-butylanisol sold by Eastman Kodak under the commercial name "TENOX BHA") | 0.15 g |
| C.I. Basic Violet 1 | 0.0012 g |
| Water sufficient for | 100 cc |

This hair-setting solution, applied to bleached wet hair, gives, after drying, a bluish glint to the hair.

EXAMPLE 2

A colored hair-setting lotion of the following composition is prepared:

| | |
|---|---|
| Vinylpyrrolidone/vinyl acetate copolymer 70%/30% (M.W. 40,000 to 400,000) | 2 g |
| Ethanol sufficient for 50° | |
| Triethanolamine, sufficient for pH 7 | |
| Butylhydroxyanisole: (Mixture of 4-hydroxy 3-t-butylanisole and 4-hydroxy 2-t-butylanisole sold by Eastman Kodak under the commercial name "TENOX BHA") | 0.15 g |
| Dodecyl gallate | 0.03 g |
| Benzylidene camphor | 0.2 g |
| C.I. Acid Black 2 | 0.01 g |
| Water sufficient for | 100 cc |

This hair-setting lotion, applied to wet, dyed hair, gives, after drying, a bluish gray glint to the hair.

EXAMPLE 3

A hair-setting lotion of the following composition is prepared:

| | |
|---|---|
| Vinylpyrrolidone/vinyl acetate copolymer 70%/30% (M.W. 40,000 to 400,000) | 2 g |
| Ethanol sufficient for 50° | |
| Butylhydroxyanisole: (Mixture of 4-hydroxy 3-t-butylanisol and 4-hydroxy 2-t-butylanisol sold by Eastman Kodak under the commercial name "TENOX BHA") | 0.2 g |
| Water sufficient for | 100 cc |

This hair-setting lotion, applied to wet hair, previously dyed with an oxidation dye, assures a better holding to the coloring.

EXAMPLE 4

A hair-setting lotion of the following composition is prepared:

| | |
|---|---|
| Crotonic acid/vinyl acetate copolymer 10%/90% (M.W. 45,000 to 70,000) | 2 g |
| Isopropanol sufficient for 50° titer | |
| Triethanolamine sufficient for pH 8 | |
| Butylhydroxyanisole: (Mixture of 4-hydroxy 3-t-butylanisol and 4-hydroxy 2-t-butylanisol sold by Eastman Kodak under the commercial name "TENOX BHA") | 0.15 g |
| Benzylidene camphor | 0.2 g |
| Benzophenone | 0.06 g |
| C.I. Acid Violet 56 | 0.05 g |
| C.I. Acid Blue 156 | 0.08 g |
| Water sufficient for | 100 cc |

The hair-setting lotion, applied to wet hair, dyed blond, gives, after drying, an ashen glint to the hair.

EXAMPLE 5

The following comparative tests were made wherein, on the one hand there was utilized a hair-setting lotion containing dodecyl gallate as a reducing agent (in accordance with the present invention) which hair-setting lotion was applied subsequent to a hair bleaching operation using $H_2O_2$ and prior to a hair dyeing operation, and on the other hand there was employed a hair-setting lotion containing pyruvic acid as a reducing agent, which latter hair-setting lotion was also applied subsequent to essentially the same hair bleaching operation using $H_2O_2$ and prior to essentially the same hair dyeing operation.

Each of the tests include three following operations, i.e.:

I. A bleaching operation effected exactly under the same conditions for each of three samples of hair;

II. A hair-setting operation for each of the three hair samples bleached in accordance with operation I wherein
1. Hair sample (a) was set using a composition containing, as a reducing agent, dodecyl gallate,
2. Hair sample (b) was set using a composition exactly the same as in (1) except that it contained, as the reducing agent, pyruvic acid,
3. Hair sample (3) was set using a composition exactly the same as in (1) except that no reducing agent was employed, and III. A hair dyeing operation, effected exactly in the same manner for each of the three hair samples (a), (b) and (c) each of which had previously been subjected to operations I and II.

Specifically each of the tests were conducted as follows:

I. Hair bleaching operation:

Three samples of natural grey hair, each weighing about 0.5 g were each bleached with 3 ml of the following hair bleaching composition:

| | |
|---|---|
| Sodium persulfate | 90 g |
| $H_2O_2$ (20 volumes) | 300 ml |
| Ethylenediamine tetra acetic acid | 0.6 g |
| Ammonia | 30 ml |

Each sample of hair was left in contact with the bleaching composition for 45 minutes. Thereafter, without neutralizing the $H_2O_2$ each sample was abundantly rinsed with water and dried.

II. Hair setting operation:

The hair setting operation for (a), (b) and (c) hair samples is carried out utilizing the following hairsetting lotions:

| | |
|---|---|
| For hair sample (a): | |
| Solution (a): | |
| Polyvinyl pyrrolidone - K30 | 1.5 g |
| Dodecyl gallate (M/1000) | 0.34 g |
| Ethyl alcohol (96°) | 40 g |
| Triethanolamine, q.s.p. | pH 7 |
| Water, q.s.p. | 100 g |
| For Hair sample (b): | |
| Solution (b): | |
| Polyvinyl pyrrolidone - K30 | 1.5 g |
| Pyruvic acid (M/1000) | 0.09 g |
| Ethyl alcohol (96°) | 40 g |
| Triethanolamine, q.s.p. | pH 7 |
| Water, q.s.p. | 100 g |
| For Hair sample (c): | |
| Solution (c): | |
| Polyvinyl pyrrolidone - K30 | 1.5 g |
| Ethyl alcohol (96°) | 40 g |
| Triethanolamine, q.s.p. | pH 7 |
| Water, q.s.p. | 100 g |

Each of the non-neutralized bleached hair samples described above is immersed in 10 ml of its respective hair-setting lotion. Essentially equal molar concentrations of dodecyl gallate and pyruvic acid are employed so as to provide a true comparison. The time of contact of each sample with its respective hair setting lotion was 20 minutes. Thereafter each hair sample was rinsed and dried.

III. Dyeing operation:

A hair dye composition was prepared by admixing the following components:

| | |
|---|---|
| 1-diamino-2-nitro-4-aminoethylamino benzene hydrobromide | 0.1 g |
| Ammonium lauryl sulfate | 20 g |
| Triethanolamine, q.s.p. | pH 8.5 |
| Water, q.s.p. | 100 g |

Each of three hair samples (a), (b) and (c) previously treated with its aforesaid respective hairsetting lotion was then dyed with 2 ml of the above hair dye composition, the time of contact of the hair dye composition for each hair sample being 40 minutes. This hair dyeing operation was carried out, in each instance, at a temperature of 37° C.

Each dyed hair sample was then rinsed, shampooed, rinsed again and dried under the same conditions. The following results were observed. The colorations achieved were compared using the Nickerson formula and the Munsell standards as indicated in the article by Dorothy Nickerson, in the Journal of the Optical Society, American, Vol. 39, 1944, pp. 550 to 570 wherein a coloration is defined by the formula:

| Coloration = H | V/C |
|---|---|
| (shade) | clarity/purity | and for each of the respective hair samples (a), (b) and (c) the coloration is as follows:

| | H | V/C |
|---|---|---|
| (a) with dodecyl gallate | 7.5 R | 6.5/4.5 |
| (b) with pyruvic acid | 8.75 R | 6.75/4.5 |
| (c) no reducing agent | 9.5 R | 6.75/4.5 | wherein R, in each instance, indicates red.

The variation in the shade obtained, on the one hand between samples (a) and (c) and, on the other hand between samples (b) and (c) is obtained by applying the Nickerson formula:

$$dE = (0.4 \, C_o dH) = (6 \, dV) + (3 \, dC)$$

wherein dE = the variation in shade, and $C_o$ is the purity of the shade taken as the basis and which is, in each instance, 4.5. The following comparative results were obtained:

1. Between samples (a) and (c)

$$dE = [0.4 \times 4.5 \times (9.5 - 7.5)] + [6 \times (6.75 - 6.5)] + [3 \times (4.5 - 4.5)] = 5.1$$

2. Between samples (b) and (c)

$$dE = [0.4 \times 4.5 \times (9.5 - 8.75)] + [6 \times (6.75 - 6.75)] + [3 \times (4.5 - 4.5)] = 1.35$$

It can be seen from the above results that sample (a) has been strikingly improved over that of sample (b) when each is compared to the control sample (c), none of the hair samples prior to the dyeing operation having been treated so as to neutralize the residual $H_2O_2$ with which each sample was contracted during the bleaching operation. From a comparison of the values obtained, i.e. 5.1 vs 1.35, it can be seen that the use of dodecyl gallate as a reducing agent in the hair-setting composition of the present invention is unexpectedly far superior to that using the pyruvic acid of the prior art.

What is claimed is:

1. A hair coloring and hair-setting lotion composition having a pH of about 5–8.5 for bleached hair or hair dyed with an oxidation dye consisting essentially of a solution of a cosmetic film forming resin having a molecular weight of about 10,000 – 400,000, a reducing agent selected from the group consisting of butyl hydroxy anisole, dodecyl gallate, propyl gallate and octyl gallate, a direct dye and a solar filter selected from the group consisting of benzylidene camphor, glyceryl paraamino benzoate, benzophenone and ethyl paradimethylamino benzoate, in an aqueous lower alkanol solvent wherein said lower alkanol contains 1–4 carbon atoms and is present in an amount of about 20 to 50 percent by weight of said composition, said reducing agent being present in an amount of about 0.02 to 2 percent by weight of said composition, said cosmetic film forming resin being present in an amount of about 1 to 3 percent by weight of said composition, said direct dye being present in an amount of about 0.001 to 0.1 percent by weight of said composition and said solar filter being present in an amount of about 0.03 to 2 percent by weight of said composition.

2. The composition of claim 1 wherein said cosmetic film forming resin is polyvinylpyrrolidone having a molecular weight of 40,000–400,000.

3. The composition of claim 1 wherein said cosmetic film forming resin is a copolymer of vinylpyrrolidone and vinyl acetate, 70%:30% to 30%:70%, having a molecular weight of 40,000–400,000.

4. The composition of claim 1 wherein said cosmetic film forming resin is a copolymer of crotonic acid and vinyl acetate, 10%:90%, having a molecular weight of 45,000–70,000.

5. A method for treating peroxide-containing human hair for neutralizing the peroxide therein comprising contacting said peroxide-containing hair with an effective amount to neutralize said peroxide of a solution of a cosmetic film forming resin having a molecular weight of about 10,000–400,000, a reducing agent selected from the group consisting of butyl hydroxy anisole, dodecyl gallate, propyl gallate and octyl gallate, a direct dye and a solar filter selected from the group consisting of benzylidene camphor, glyceryl paraamino benzoate, benzophenone and ethyl paradimethylamino benzoate, in an aqueous lower alkanol solvent wherein said lower alkanol contains 1–4 carbon atoms and is present in an amount of about 20 to 50 percent by weight of said composition, said reducing agent being present in an amount of about 0.02 to 2 percent by weight of said composition, said cosmetic film forming resin being present in an amount of about 1 to 3 percent by weight of said composition, said direct dye being present in an amount of about 0.001 to 0.1 percent by weight of said composition and said solar filter being present in an amount of about 0.03 to 2 percent by weight of said composition.

* * * * *